United States Patent [19]
Borders, Jr.

[11] Patent Number: 5,320,637

[45] Date of Patent: Jun. 14, 1994

[54] SAFETY SKIN HOOK AND METHOD

[76] Inventor: Jack C. Borders, Jr., 7905 Ardmore Ave., Baltimore, Md. 21234

[21] Appl. No.: 73,158

[22] Filed: Jun. 7, 1993

[51] Int. Cl.$^5$ .................. A61B 17/28; A61B 17/02
[52] U.S. Cl. ................... 606/207; 606/205; 128/20
[58] Field of Search ............. 606/205–211; 128/17, 20

[56] References Cited

U.S. PATENT DOCUMENTS

| | | | |
|---|---|---|---|
| 943,263 | 12/1909 | Moraweck | 606/205 |
| 1,601,035 | 9/1926 | Nauth | 128/20 |
| 2,070,670 | 2/1937 | Marshall | 128/20 |
| 3,035,582 | 5/1962 | Seiger | 606/205 |
| 3,470,872 | 10/1969 | Grieshaber | 128/17 |
| 3,779,248 | 12/1973 | Karman | 128/17 |
| 3,857,386 | 12/1974 | Ashbell | |
| 3,911,925 | 10/1975 | Tillery, Jr. | 606/208 |
| 4,574,805 | 3/1986 | Lerner | |
| 4,621,619 | 11/1986 | Sharpe | |
| 4,865,019 | 9/1989 | Phillips | 128/20 |
| 5,222,951 | 6/1993 | Abidin et al. | 128/20 |

FOREIGN PATENT DOCUMENTS 836545 4/1952 Fed. Rep. of Germany ...... 606/208
820618 11/1937 France .................. 128/20

OTHER PUBLICATIONS

The Lawton Company, *Surgical Instrument Catalog*, New York, N.Y., pp. 15, 17, 38–40, 61, 76, 77, 145, 290, ©1957.
V. Mueller & Co., *A Comprehensive Guide to Purchasing*, Rochester, Minn., pp. 197–200, 214 and 481, ©163.
Richards Medical Co., Ear, Nose, Throat and Specialty Surgical Instruments Catalog, pp. 55 and 107, ©1987, Memphis, Tenn.

*Primary Examiner*—Ralph Lewis
*Attorney, Agent, or Firm*—Pravel, Hewitt, Kimball & Krieger

[57] ABSTRACT

The invention relates to an instrument for holding skin at an incision site having two pivotally connected elongated members, each member having releasably engagable handles while one member has a hook and the other has a paddle. The hook can be moved into and out of proximity with the paddle for shielding the hook when it is in close proximity to the paddle.

7 Claims, 2 Drawing Sheets

SAFETY SKIN HOOK AND METHOD

BACKGROUND OF THE INVENTION

1. Field of the Invention

This invention relates to a device and a method for hooking skin and holding it away from an incision, thus affording a surgeon greater access to the surgical area. More particularly, a forceps-type instrument is configured to hook into the skin on one side of an incision and hold the skin back against the hook.

2. Description of the Related Art

The invention relates to a device for hooking and, holding back the skin at an incision in the skin surface. An incision tends to remain closed because of the resilience of the skin and underlying tissue. Skin hooks are used to counteract this tendency by hooking the skin for the purpose of pulling the skin back from the incision and for providing a surgeon with improved access and visibility.

Known devices of this type include straight-shaft skin hooks, which have a pencil-type shape, with single or multiple hooks, as described and shown in U.S. Pat. No. 3,857,386 to Ashbell. Skin hooks of this design suffer from several disadvantages including the fact that they tend to slip to an extent that the hook becomes dislodged and needs to be reinserted. These skin hooks may also cause trauma from slippage in that the skin may tear in the area where the hook has slipped. More importantly, since the hook is not covered or protected, the physician or attendant is at significant risk of being inadvertently punctured, particularly when the skin hook is passed from the attendant to the physician or vice versa. With the possibility that these medical professionals could become infected by viruses such as AIDS or hepatitis from such a puncture, this design has severe disadvantages. Hooks with this design are also subject to being bent out of shape because the tips are unprotected, requiring frequent replacement.

Adhesive retractors for retracting skin at the edges of an incision, such as described and shown in U.S. Pat. No. 4,621,619 to Sharpe, have also been used to address the problem of slippage. An adhesive pad enables the retractor to remain in place. These products have drawbacks such as adhesives that do not stick all the time and the fact that they are not reusable which contributes to higher medical costs and waste that requires special handling. Further, since sterility is of utmost importance during an operation, the adhesive retractor is disadvantageous because it is difficult to sterilize since the adhesive pads are not autoclavable. Neither do adhesive retractors protect against accidental puncture by the retractor hooks.

Thus, there exists a need for a skin hook that will not slip, causes minimum trauma to the patient, will not bend when inadvertently bumped or dropped, and does not have unshielded sharp points or edges that could accidentally puncture physicians or attendants engaged in surgical procedures.

SUMMARY OF THE INVENTION

The subject invention relates to a skin hook device which has a pair of opposable members that are connected at a common pivot point, each member having a handle portion capable of being locked in position and an elongated leg portion. One of the leg portions has a hook formed on its outer end, and the other has a paddle-shaped end section positioned to cooperate with the hook. When the members are moved about the pivot point, the hook can be positioned adjacent to the paddle-shaped section.

With this design, a surgeon presented with an incision can hook the skin at the incision and pull the skin away from the incision for access to the surgical area. The improved skin hook effectively holds the skin away from an incision with little trauma since the paddle is positioned to oppose the hooked skin when the members are locked into place, thus maintaining the skin hook in place.

The paddle in proximity with the hook protects surgeons and their attendants from inadvertent puncture of their skin by the hook during surgery and when the instrument is being handled. This is especially important during or after a surgical procedure when the hook is often covered in blood or other bodily fluids that could transmit bacterial or viral disease. The useful life of the instrument is also extended because the hook is protected by the paddle during sterilization and handling, which reduces the risk of damaging the ends of the hook.

BRIEF DESCRIPTION OF THE DRAWINGS

A better understanding of the invention can be obtained when the detailed description of an exemplary embodiment set forth below is considered in conjunction with the attached drawings, in which.

DESCRIPTION OF EXEMPLARY EMBODIMENTS

Figure 1:
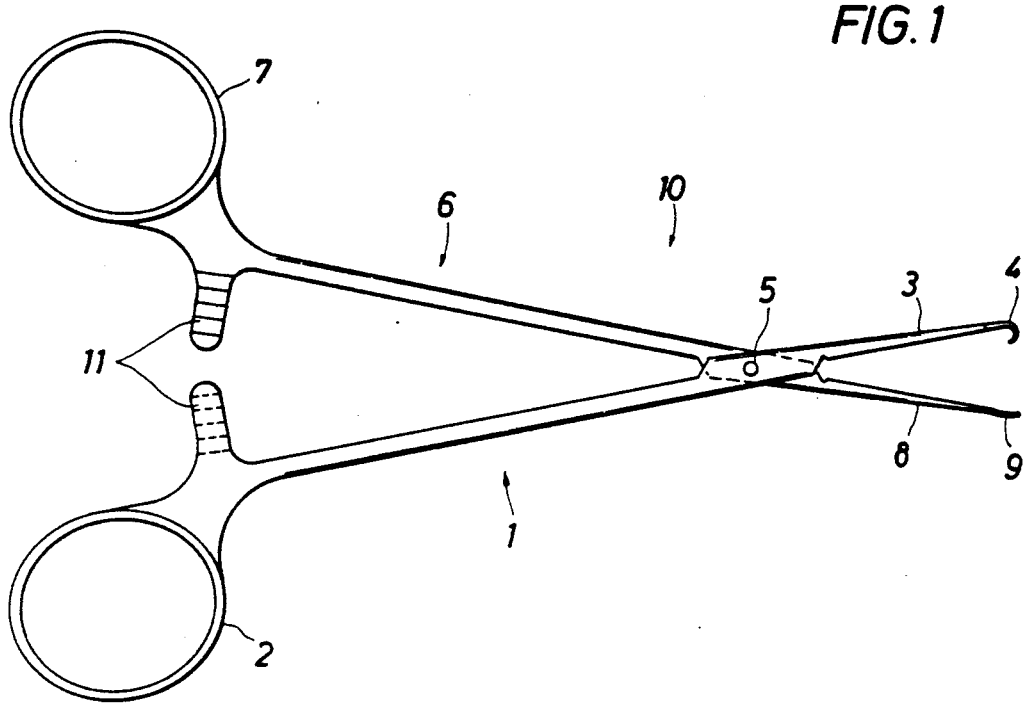
FIG. 1 is a top plan view of the instrument of the present invention.

FIG. 1 shows an embodiment of a skin hook instrument 10 made in accordance with the invention. The instrument 10 includes a first member 1 which has a handle 2 at one end, and a leg 3 at the other end terminating with a two-pronged hook 4. A second member 6 has a handle 7 at one end, and a leg 8 at the other end terminating with a paddle 9. The members 1, 6 are pivotally connected to each other at a pivot point 5 (commonly referred to as a "box lock") and are capable of moving relative to one another in a single plane about the pivot point 5.

In a preferred embodiment, the handles 2,7 may be formed with smooth, circular finger rings that permit the instrument to be manipulated by the surgeon with a thumb and one finger.

The handles 2,7 also include a known, releasably-engaging ratcheting mechanism in the form of opposing serrated faces 11, which upon closure of the handles 2,7, force the interlocking of the serrated faces 11. When the handles are in this position (see FIG. 5), they are held together and prevented from opening as described in greater detail below. The ability to releasably engage the handles 2,7 relative to one another enables the hook 4 and the paddle 9 to be held in proximity to one another, permitting the paddle 9 to shield the surgeon and attendants from an inadvertent puncture by the hook 4. This is an important feature of the invention because during surgery the hook 4 is often covered in blood or other bodily fluids that could transmit disease.

Also, the proximity of the hook 4 and the paddle 9, held together by releasably engaging the handles 2,7 enables the device 10 to hold the skin at the incision back and firmly in place by squeezing the skin in a sandwich type fashion between the hook 4 and the paddle 9. Such an arrangement permits less slippage than a single-handled device.

Figure 2:
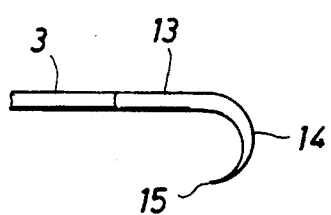
FIG. 2 is a side plan view of the hook portion of the instrument of FIG. 1.
Figure 2A:
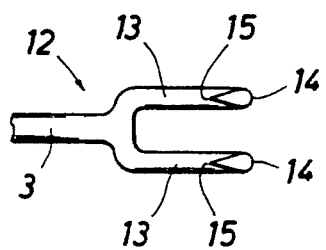
FIG. 2A is a bottom plan view of the hook portion shown in FIG. 2.

A preferred embodiment of the hook 4 is shown on FIGS. 2 and 2A where a two-pronged hook 12 has two shanks 13, generally in-line with the leg 3. Each shank 13 has a C-shaped bend 14 terminating in a sharp-tipped end 15. The ends 15 are sharp enough to penetrate the patient's skin and serves as an effective mechanism for hooking and holding back the skin at an incision. The ends 15 may have smooth tips as shown or one or more barbs (not shown) on it to facilitate holding the skin.

The hook 4 may also be formed as a single hook or multiple hooks of varying curvature, spacing and dimension to facilitate the hooking and holding of the skin in different positions. In the preferred embodiment shown in FIGS. 2 and 2A, the bends 14 are formed such that the ends 15 are curved so they extend parallel to the shanks 13. This shape aids in hooking the skin at the incision and pulling it back. Most preferably, the bend 14 and sharp-tipped end 15 are designed to form a curved arc having an angle of between about 120°–180° from the shank 13, the embodiment in FIG. 2 being formed at an angle of about 180°.

Figure 3:
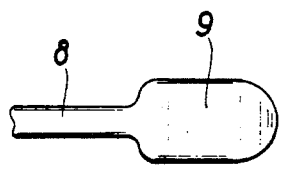
FIG. 3 is a top plan view of the paddle-shaped end of the instrument of FIG. 1.
Figure 3A:
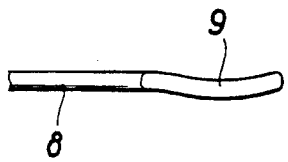
FIG. 3A is side plan view of the paddle-shaped end shown in FIG. 3.

FIGS. 3 and 3A show a preferred embodiment of the paddle 9 as a relatively smooth surface extension of the leg 8 of the second member 6. As shown in FIG. 3A, the paddle 9 is slightly curved to receive the hooked skin as described below and shown in FIG. 5, and to help avoid accidental punctures. When the paddle 9 and hook 4 are adjacent to each other as shown, they are capable of securely holding the skin at an incision without slippage. Also, when the paddle 9 covers the hook 4 as shown, it protects surgeons and attendants from skin punctures by the hook 4 during surgical procedures. The paddle 9 also protects the hook 4 from being inadvertently hit or snagged to prevent the ends 15 from breaking or bending.

The paddle 9 may be formed in a variety of shapes, sizes or curvatures. In a preferred embodiment, the paddle 9 should extend beyond and cover the hook 4. Preferably, the paddle 9 is about 0.5 mm to about 1.5 mm thick, about 2.0 mm to about 10.0 mm wide, and about 3.0 mm to about 14.0 mm long.

Figure 4:
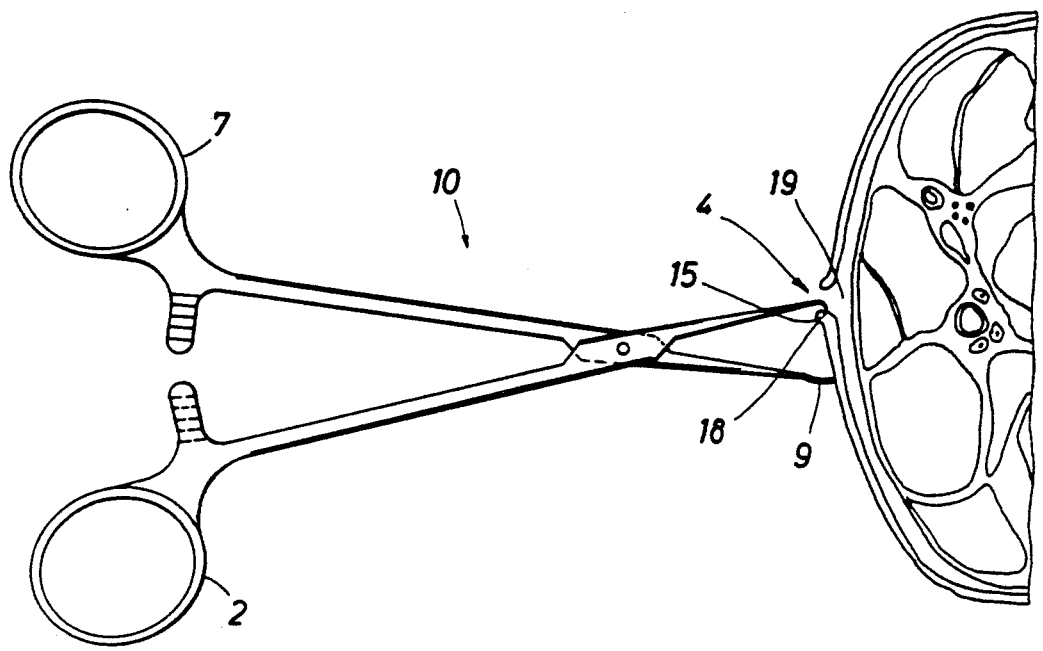
FIG. 4 is a perspective view of the instrument of FIGS. 1-3, showing the instrument at the site of an incision.
Figure 5:
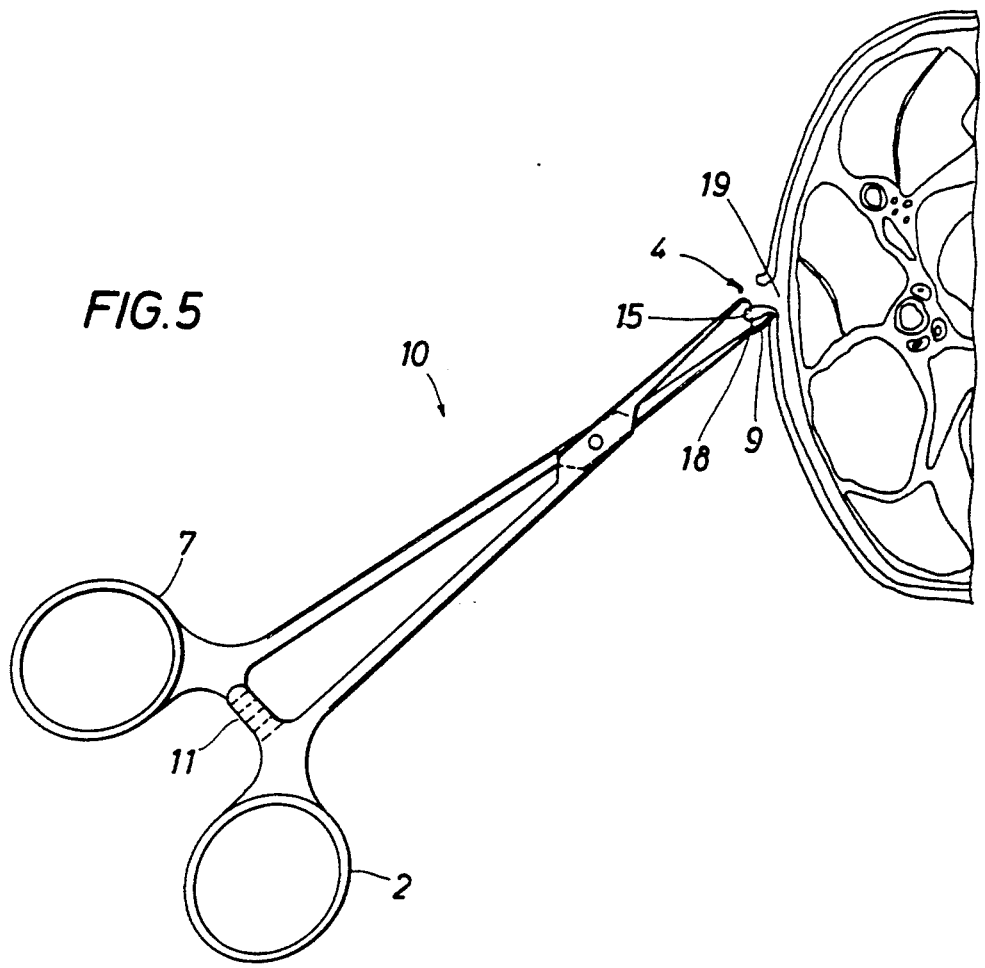
FIG. 5 is a perspective view of the instrument of FIGS. 1-3, showing the skin at an incision sandwiched between the hook portion and the paddle-shaped end.

FIGS. 4 and 5 show how the skin hook instrument 10 engages and retracts skin 18 from underlying tissue 19 at an incision site. After an incision is formed, the surgeon inserts the sharp-tipped ends 15 into the skin adjacent to the incision. Once engaged, the hook 4 is used to pull the skin 18 away from the incision. As the handles 2,7 are pivoted towards each other, the paddle 9 and the hook 4 operate to sandwich the skin 18, so that the skin 18 is held securely between the paddle 9 and the hook 4, exposing the underlying tissue 19. When the skin 18 has been pulled back to a position as shown in FIG. 5, the serrated faces 11 are engaged to hold the instrument in place. This operation of the instrument 10 is advantageous because the skin 18 is held securely in place, reducing trauma to the patient because the skin is not torn due to slippage or re-engagement of the hook 4 after slippage. The instrument 10 is then laid back against the skin away from the incision for achieving maximum exposure to the surgical area.

As previously indicated, many variations may be made to the device 10 without deviating from the broader aspects of the invention. For example, while the preferred form of the invention utilizes stainless steel for construction of the instrument, other autoclavable materials can be used. The inner surface of the finger rings may be irregular in shape such as, for example, by forming closely spaced ridges (not shown) that facilitate a firm grasp by the surgeon. The handles 2,7 can be releasably engaged by other known mechanisms, and the handles 2,7 may be bent at various angles to facilitate access to the surgical area. The surface of the paddle 9 facing the hook 4 may be transversely scored to form closely spaced ridges that will facilitate the holding of the skin at the incision (not shown).

The instrument 10 solves the problems mentioned above by providing a skin hook which does not slip when it is in place, and which will not accidentally puncture physicians or attendants engaged in surgical procedures.

Having described the invention above, various modifications of the techniques, procedures, material and equipment will be apparent to those skilled in the art. It is intended that all such variations within the scope and spirit of the invention be included within the scope of the appended claims.

I claim:

1. An instrument for holding skin at an incision site, comprising:
    a first elongated member having a handle at one end and a leg at the other end terminating in a hook having at least one C-shaped bend extending from the first leg and having a sharp-tipped end and an arc of between about 120° to about 180°;
    a second elongated member having a handle at one end and a leg at the other end terminating in a paddle;
    means for pivotally connecting said first and second member so that said hook can be moved into and out of proximity with said paddle for shielding the hook when it is in close proximity to the paddle; and
    means for releasably engaging said first and second handles.

2. The instrument of claim 1, wherein the paddle has a face that is slightly curved for conforming to the shape of the hook.

3. The instrument of claim 1, wherein the means for releasably engaging the first and second handles comprises the first handle having a first serrated face, the second handle having a second serrated face, and said first serrated face and said second serrated face being releasably engagable.

4. The instrument of claim 1, wherein the paddle is about 2.0 mm to about 10.0 mm wide, and about 3.0 mm to about 14.0 mm long.

5. The instrument of claim 1, wherein the means for pivotally connecting the first and second members is located between the handle and the leg on both the first and second members.

6. A method for holding back skin adjacent an incision to provide a surgeon improved access to tissue and bone beneath the incision, comprising the steps of:

selecting an instrument for holding skin at an incision site having a first elongated member having a handle at one end and a leg at the other end terminating in a hook having at least one C-shaped bend and having a sharp-tipped end and an arc of between about 120° to about 180°; a second elongated member having a handle at one end and a leg at the other end terminating in a paddle; means for pivotally connecting said first and second members so that said hook can be moved into and out of proximity with said paddle for shielding the hook when it is in close proximity to the paddle; and means for releasably engaging said first and second handles;

aligning the instrument on one side of the incision with the hook adjacent the incision and the paddle located away from the incision;

hooking the hook into the skin at the incision;

pivoting the paddle against the outer surface of the skin, opposing the hook; and engaging the means for releasably engaging the first and second handles such that the skin is held back from the incision.

7. The method of claim 6, wherein when engaging the means for releasably engaging the first and second handles, the paddle is brought within about 1.0 mm to about 2.5 mm of the hook.

* * * * *